(12) United States Patent
Green, II et al.

(10) Patent No.: US 10,285,716 B2
(45) Date of Patent: May 14, 2019

(54) MIDLINE REFERENCING FEMORAL SIZING CALIPER

(71) Applicant: MICROPORT ORTHOPEDICS HOLDINGS INC., Tiel (NL)

(72) Inventors: John Michael Green, II, Arlington, TN (US); Brian Robert Harris, Jr., Cordova, TN (US)

(*) Notice: Subject to any disclaimer, the term of this patent is extended or adjusted under 35 U.S.C. 154(b) by 0 days.

(21) Appl. No.: 15/877,642

(22) Filed: Jan. 23, 2018

(65) Prior Publication Data

US 2018/0146971 A1 May 31, 2018

Related U.S. Application Data

(63) Continuation of application No. 15/180,966, filed on Jun. 13, 2016, now Pat. No. 9,872,690, which is a continuation of application No. 14/179,003, filed on Feb. 12, 2014, now Pat. No. 9,364,346, which is a continuation of application No. 13/540,782, filed on Jul. 3, 2012, now Pat. No. 8,652,144, which is a continuation of application No. 12/488,252, filed on Jun. 19, 2009, now Pat. No. 8,216,244.

(51) Int. Cl.
*A61B 17/17* (2006.01)
*A61F 2/46* (2006.01)
*A61F 2/38* (2006.01)

(52) U.S. Cl.
CPC ........ *A61B 17/1764* (2013.01); *A61F 2/4657* (2013.01); *A61F 2/3859* (2013.01); *A61F 2002/4658* (2013.01); *A61F 2002/4661* (2013.01)

(58) Field of Classification Search
CPC ....... A61B 17/17; A61B 17/1764; A61F 2/46; A61F 2/4657
See application file for complete search history.

(56) References Cited

U.S. PATENT DOCUMENTS

| | | | | |
|---|---|---|---|---|
| 5,662,656 A * | 9/1997 | White | ................. | A61B 17/155 606/86 R |
| 5,916,220 A * | 6/1999 | Masini | ................. | A61B 17/155 606/87 |
| 6,024,746 A * | 2/2000 | Katz | ................. | A61B 17/154 606/102 |

* cited by examiner

*Primary Examiner* — Christopher Beccia

(57) ABSTRACT

A sizing caliper for facilitating the selection of a femoral component of a knee prosthesis includes a caliper body, two drill guide bodies, a stylus tower configured to be slidably linked to each other wherein as the caliper body and the stylus tower are linearly displaced at an equal rate relative to the drill guide body portions and the drill guide holes remain located at the midpoint of an anterior/posterior dimension defined by the distance between the tip of the stylus and the base portion. The caliper body comprises a base portion configured to couple and decouple from the caliper body using a sliding mechanism.

15 Claims, 11 Drawing Sheets

MIDLINE REFERENCING FEMORAL SIZING CALIPER

CROSS-REFERENCE TO RELATED APPLICATIONS

This application is a continuation of U.S. patent application Ser. No. 15/180,966, filed Jun. 13, 2016, which is a continuation of U.S. patent application Ser. No. 14/179,003, filed Feb. 12, 2014, now U.S. Pat. No. 9,364,346, which is a continuation of U.S. patent application Ser. No. 13/540,782, filed Jul. 3, 2012, now U.S. Pat. No. 8,652,144, which is a continuation of U.S. patent application Ser. No. 12/488,252, filed Jun. 19, 2009, now U.S. Pat. No. 8,216,244, the disclosures of which are incorporated herein by reference in their entirety.

FIELD OF THE INVENTION

The present disclosure is related to sizing and locating a distal femoral knee prosthesis for locating and securing the prosthesis in place of the distal femur.

BACKGROUND

In order to size and position a femoral knee prosthesis, sizers or calipers are used. The conventional calipers typically follow the referencing method of how the prosthesis grows from size to size. For example, in some knee prosthesis systems, anterior referencing sizing scheme is utilized for the implants where a common anterior/posterior distance from the tip of the anterior flange and the medial/lateral stabilizer pegs (perpendicular from the distal surface of the implant) is maintained for different sizes. The anterior referencing sizing scheme requires that the sizing caliper that sizes the distal femoral implant must measure in the same manner, in which the device will maintain a common distance for drill holes referenced in later steps in the procedure and grow in the opposite direction (i.e. posterior direction).

In other knee prosthesis systems, posterior referencing sizing scheme is utilized. In the posterior referencing sizing scheme, a common anterior/posterior distance from the posterior condyles and the medial/lateral stabilizer pegs is maintained for different sizes. Similar to the anterior referencing systems, the posterior referencing system also imposes an asymmetric requirement on the sizing caliper. The sizing caliper must measure in the manner in which the caliper maintains a common distance for the drill holes referenced in later steps in the procedure and grow in the opposite direction (i.e. anterior direction).

These conventional measuring instruments are dependent on the implant systems that drive them, but create additional problems for the ones they attempt to solve. For the case of an anterior referencing system, the attempt to prevent notching the anterior cortex (a condition where an undercut is created in the anterior cortex resulting from improper posterior positioning of subsequent instruments) will create all bone resections to pull away from the posterior condyles. This can create issues with the flexion/extension gap and create a tighter implant that limits flexion or creating instability in the implant. Additionally, posterior condylar offset can be affected, resulting in conditions where the patient may not obtain as much flexion as desired by the surgeon. Conversely, for a posterior referencing implant, the attempt to maintain flexion/extension gap (and posterior condylar offset) kinematics could create a condition where the surgeon may notch the anterior cortex, thus creating a stress riser and possible fracture conditions. Additionally, malposition or inaccurate sizing of a posterior referencing system may negatively affect the patella-femoral gap, which may also impact the ability for the replaced knee to achieve full flexion or extension.

SUMMARY

According to an embodiment of the present disclosure, a sizing caliper for facilitating the selection of a femoral component of a knee prosthesis to be attached to a resected distal end of a femur is disclosed. The caliper comprises a caliper body configured for coupling to the resected distal end of the femur and be referenced to one or more of the posterior femoral condyles of the femur, a drill guide body, a stylus tower, and a graduated stylus slidably coupled to the stylus tower. The graduated stylus is configured to be placed adjacent an anterior condyle surface of the femur, wherein the caliper body, the drill guide body and the stylus tower are slidably linked to each other by a linkage pin laterally extending there through in a manner thereby when the caliper body and the stylus tower are linearly displaced in opposite directions relative to the drill guide body, the caliper body and the stylus tower are linearly displaced at an equal rate relative to the drill guide body.

The sizing caliper enables locating the referencing holes on the resected distal end of the femur for subsequent chamfer resections of the femur to be referenced from the midline of the distal end of the femur between the anterior cortex (anterior flange run-out of the distal femoral implant) and the posterior condyles rather than strictly the anterior or posterior surfaces.

BRIEF DESCRIPTION OF THE DRAWINGS

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
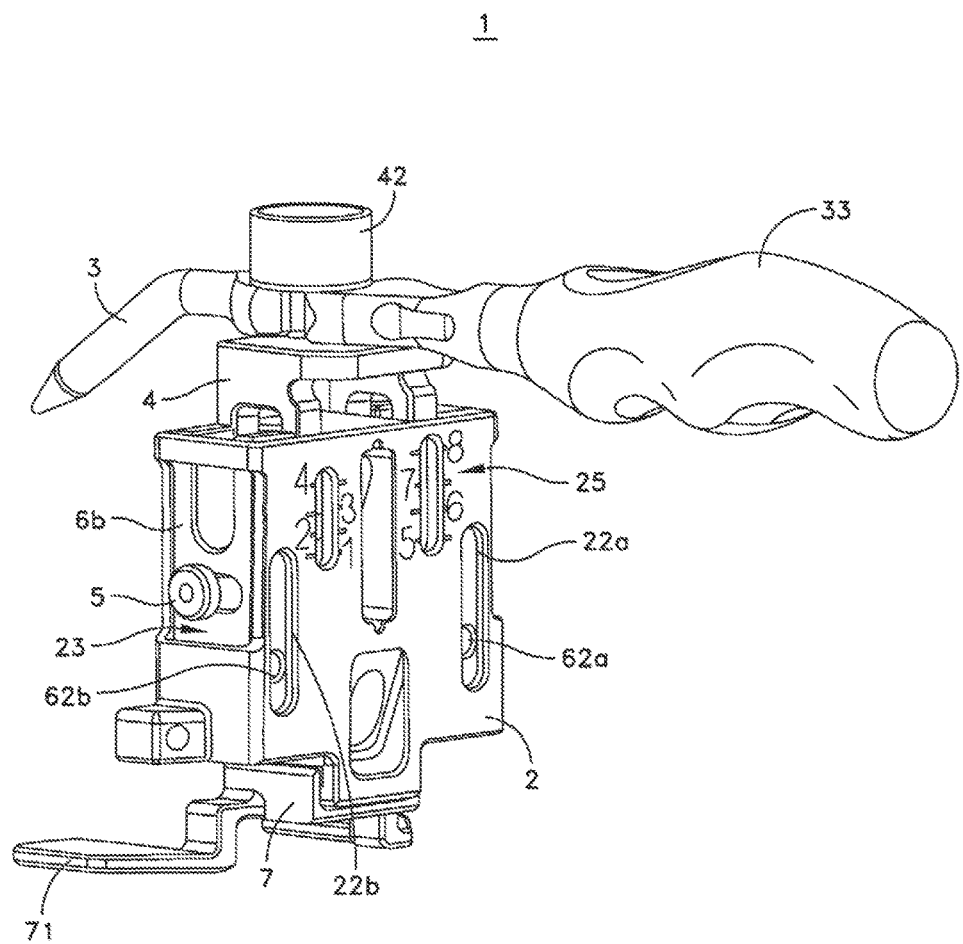
FIG. 1 is a perspective view of a femoral sizing caliper according to an embodiment of the present disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, such as "coupled", "connected" and "interconnected," refer to a relationship wherein structures are secured or attached to one another either directly or indirectly through intervening structures, as well as both movable or rigid attachments or relationships, unless expressly described otherwise.

Figure 2:
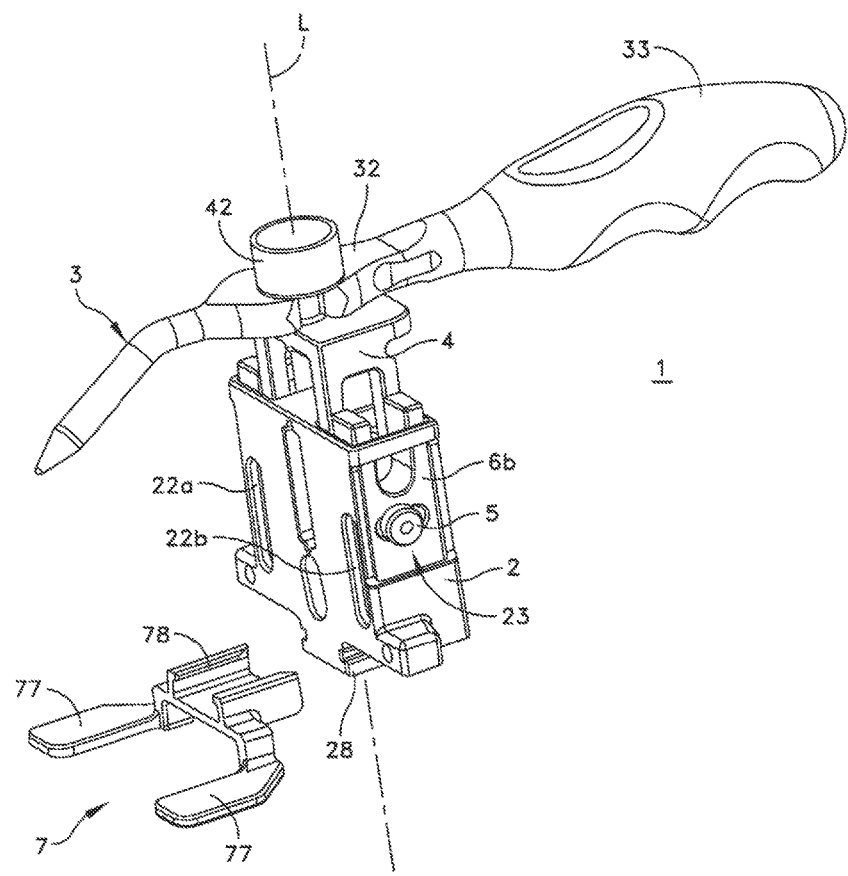
FIG. 2 is another perspective view of the sizing caliper.
Figure 3:
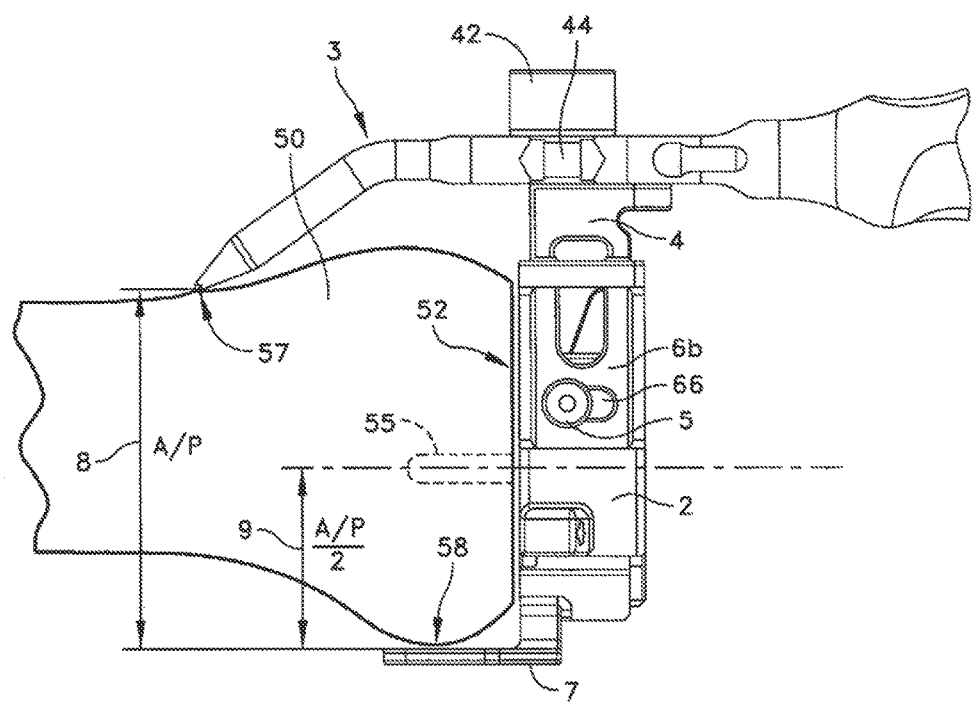
FIG. 3 is a side view of the sizing caliper fitted against a distal end of a femur 50 in a retracted position.

Referring to FIGS. 1, 2 and 3, a femoral sizing caliper 1 according to an embodiment is shown. The femoral sizing caliper 1 facilitates the selection of a femoral component of a knee prosthesis to be attached to a resected distal end 52 of a femur 50. In this embodiment, the sizing caliper 1 is a linkage assembly comprised of a caliper body 2, a stylus 3, a stylus tower 4, a linkage pin 5, drill guide body portions 6a, 6b. The caliper body 2 can further comprise a base portion 7 that is configured to be positioned adjacent to one or more of the posterior femoral condyle surfaces 58 of the femur 50 for referencing the caliper body to one or more of the posterior femoral condyles. The base portion 7 comprises paddles 77 for contacting one or more of the posterior femoral condyle surfaces 58 that establish the orientation and position of drill guide holes 62a, 62b.

FIG. 3 shows a side view of the femoral sizing caliper 1 engaging the resected distal end 52 of the femur 50. To determine the proper size for the femoral component of a knee prosthesis, the caliper body 2 is placed flush against the resected distal end 52 of the femur 50 and the caliper 1 is adjusted so that the paddles 77 of the base portion 7 rest against one or more of the posterior condyle surfaces 58 and the tip of the stylus 3 rests against the most prominent aspect 57 of the anterior cortex just proximal to the anterior condyles. The position of the tip of the stylus 3 shown in this embodiment can be adjusted by turning the stylus 3 about the pivot axle 44 of the stylus tower 4 using the handle 33. Another embodiment of stylus 3 may permit proximal translation of the stylus tip to account for the varying proximal heights of the anterior flange of the different sizes of distal femoral implants. This adjustment allows the sizing caliper 1 to be properly fitted to the femur 50 according to the anterior/posterior (A/P) dimension 8 of the femur 50 for purpose of determining the optimal size for the femoral knee component. Once the sizing caliper 1 is properly adjusted to fit the femur 50, the graduated size indicator markings 25 provided on the caliper body 2 indicates the optimal size of the femoral component of the knee prosthesis for the femur 50.

Figure 6:
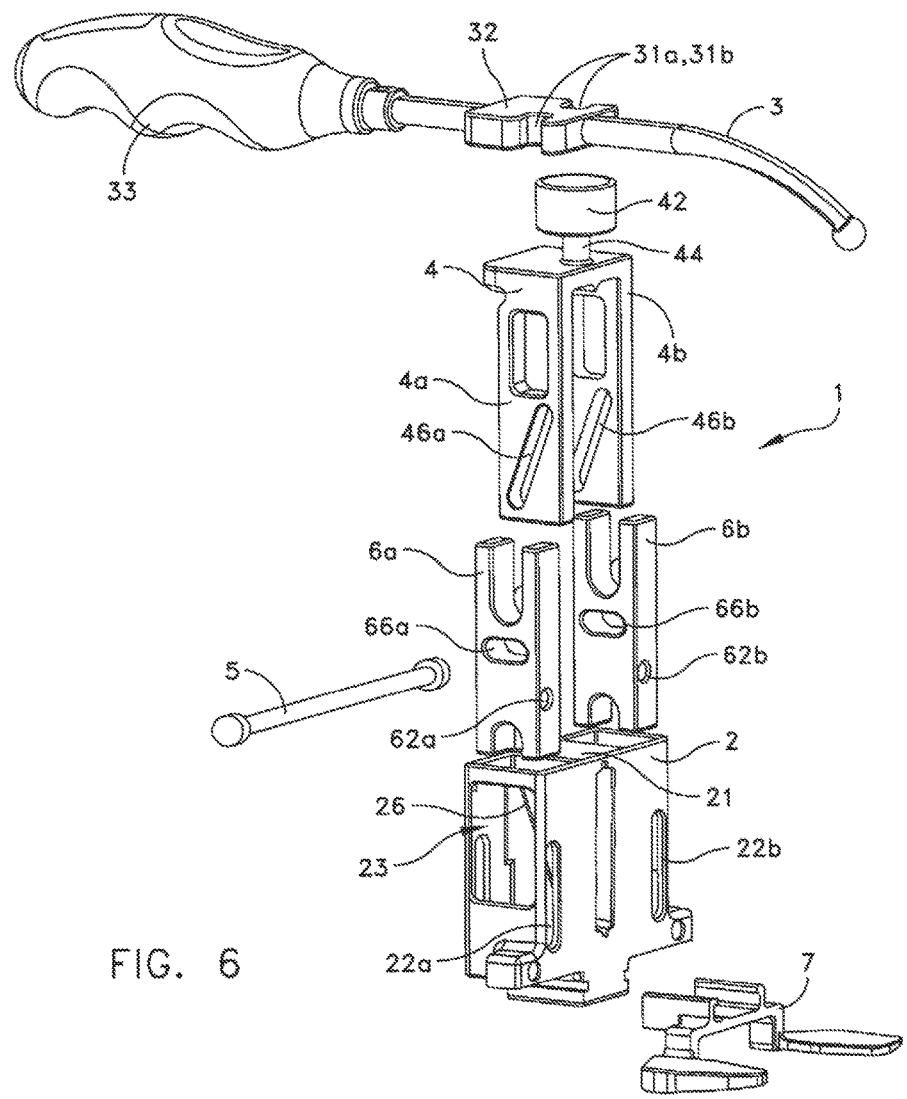
FIG. 6 is an exploded view of the sizing caliper.

As shown in FIGS. 1, 2 and the exploded view of the caliper shown in FIG. 6, the caliper body 2 is provided with openings 22a, 22b on both sides to provide access to the drill guide holes 62a, 62b provided in the drill guide bodies 6a, 6b, respectively. (See FIGS. 1 and 2). With the sizing caliper 1 properly fitted to the femur 50, referencing holes 55 are drilled into the resected distal end 52 of the femur using the drill guide holes 62a, 62b.

Figure 9:
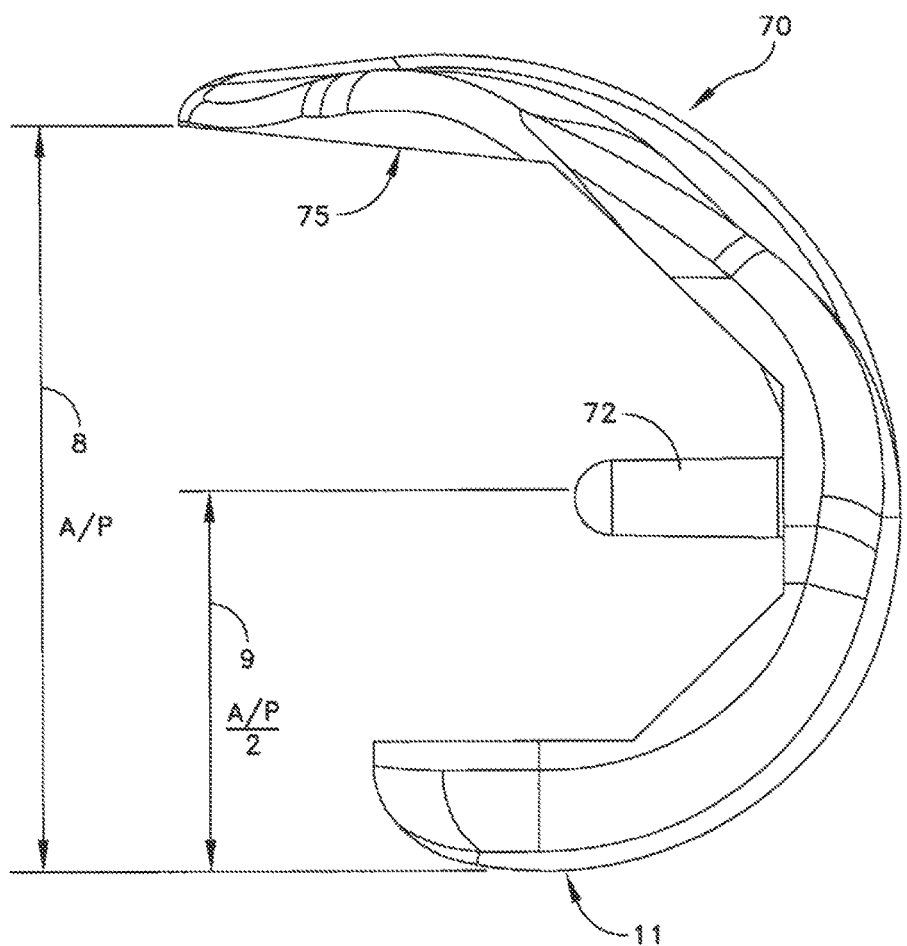
FIG. 9 is a side view of a femoral prosthesis.

After the referencing holes 55 are drilled, the caliper 1 is removed from the femur 50 and the referencing holes 55 in the resected distal end 52 of the femur 50 are used to position a resection guide (not shown) which is used to make further resections to the distal end of the femur 50. The resections form surfaces that correspond to internal planar surfaces 75 on the interior surface of a femoral component 70 of a knee prosthesis. FIG. 9 is a side view of an example of the femoral component 70 showing the internal planar surfaces 75. The femoral component 70 is provided with two medial/lateral (M/L) stabilizer pegs 72 that are inserted into the referencing holes 55 in the femur when being implanted in the patient's knee. In the conventional anterior-referencing or posterior-referencing femoral component sizing schemes, the location of the drill guide holes provided on the sizing calipers remain constant with respect to the corresponding referencing surfaces (anterior cortex or the posterior condyles). For this disclosure, the femoral component 70 is an example of a prosthetic component designed with a midline-referencing sizing scheme. The midline-referencing sizing scheme for the femoral component 70 requires that the stabilizer pegs 72 are always positioned in the middle of the A/P dimension 8 so that the distance between the center of the stabilizer pegs 72 and the posterior condyle surface 11 of the femoral component 70 is (A/P)/2 dimension 9. The sizing caliper of the present disclosure allows sizing of the distal end of the femur 50 and locating of the referencing holes 55 for receiving the stabilizer pegs 72 for the midline-referenced femoral component 70.

Unlike the sizing calipers used in the conventional sizing schemes, the sizing caliper 1 of the present disclosure allows midline-referencing sizing scheme for the femoral component 70 of the knee prosthesis. To accommodate the midline-referencing sizing scheme for the femoral component 70, the location of the drill guide holes 62a and 62b in the sizing caliper 1 with respect to the A/P dimension 8 is always at the midpoint of the A/P dimension 8.

To achieve the midline-referencing, the sizing caliper 1 is configured such that when the caliper body 2 and the stylus tower 4 are linearly displaced in opposite directions (drawn apart or brought together) relative to the drill guide body portions 6a, 6b in order to increase or decrease the A/P dimension 8, the caliper body 2 and the stylus tower 4 are linearly displaced at an equal rate relative to the drill guide body portions 6a, 6b so that the drill guide body portions 6a, 6b maintain the same relative position relative to the caliper body 2 and the stylus tower 4. Therefore, the drill guide holes 62a, 62b that are provided on the drill guide body 6 will maintain same position relative to the paddles 77 provided on the caliper body 2 and the stylus 3 on the tower 4.

Figure 4:
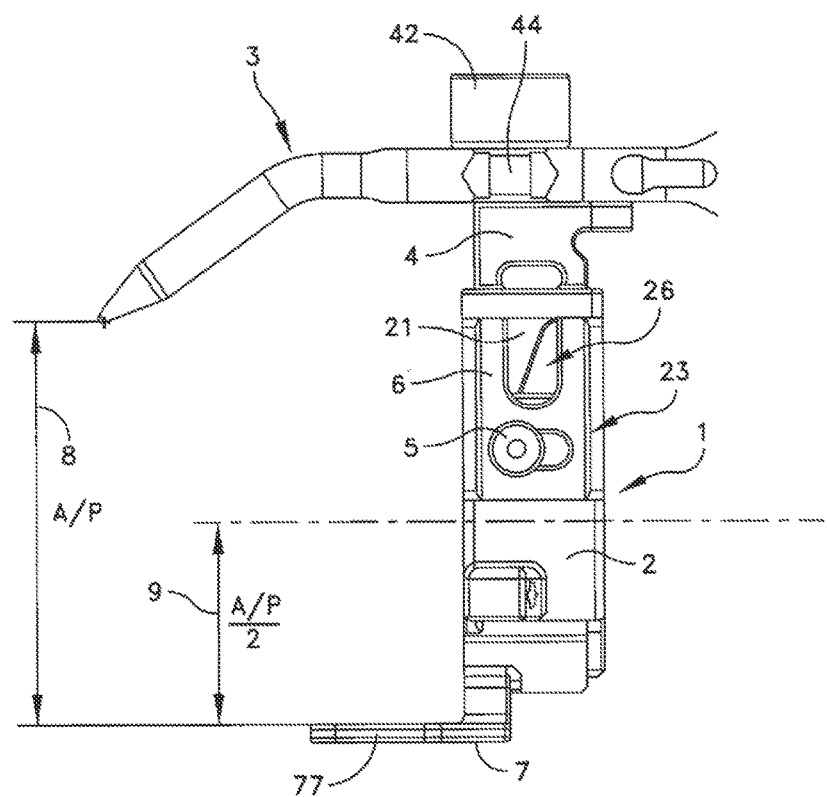
FIG. 4 is a detailed side view of the sizing caliper in the retracted position of FIG. 3.
Figure 5:
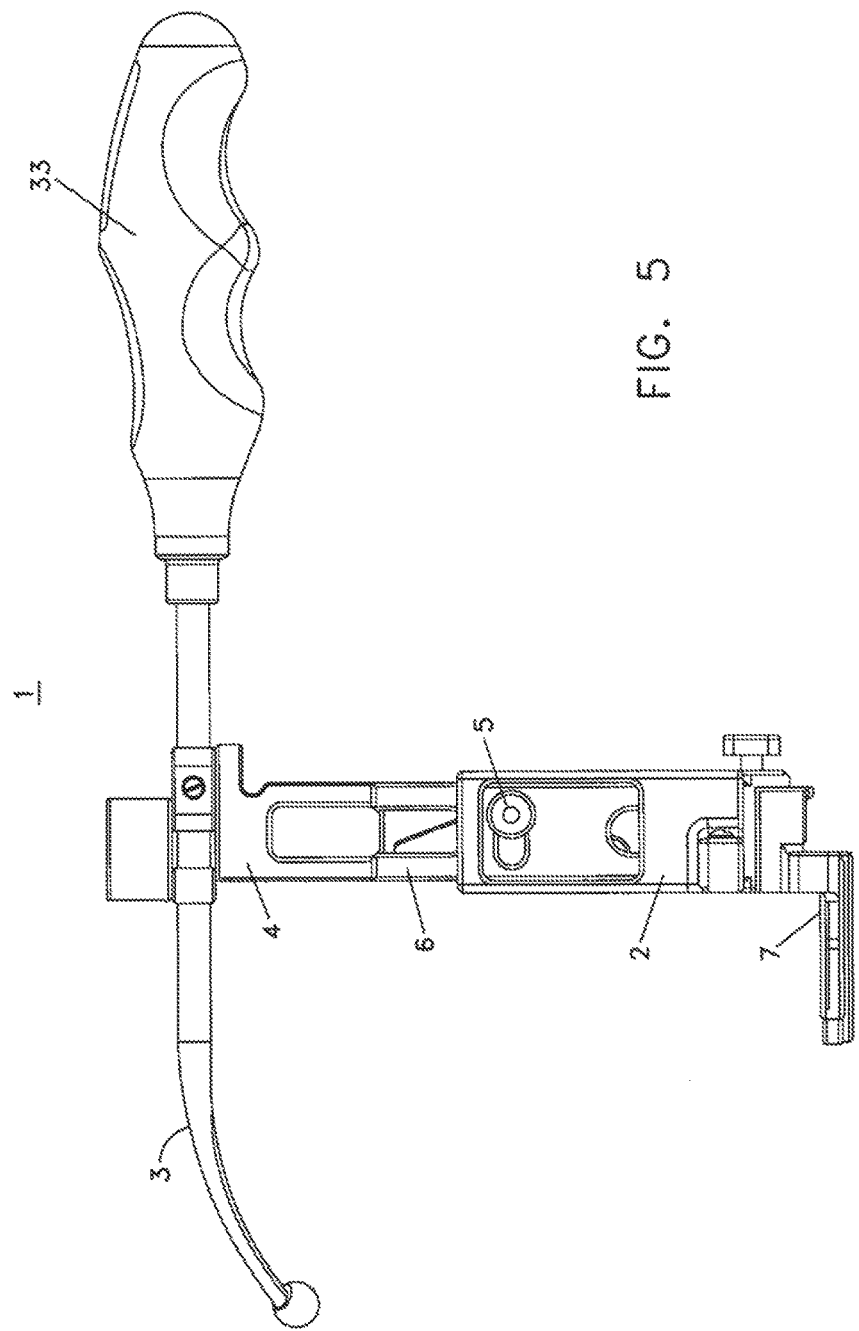
FIG. 5 is a side view of the sizing caliper in a substantially opened position.
Figure 7:
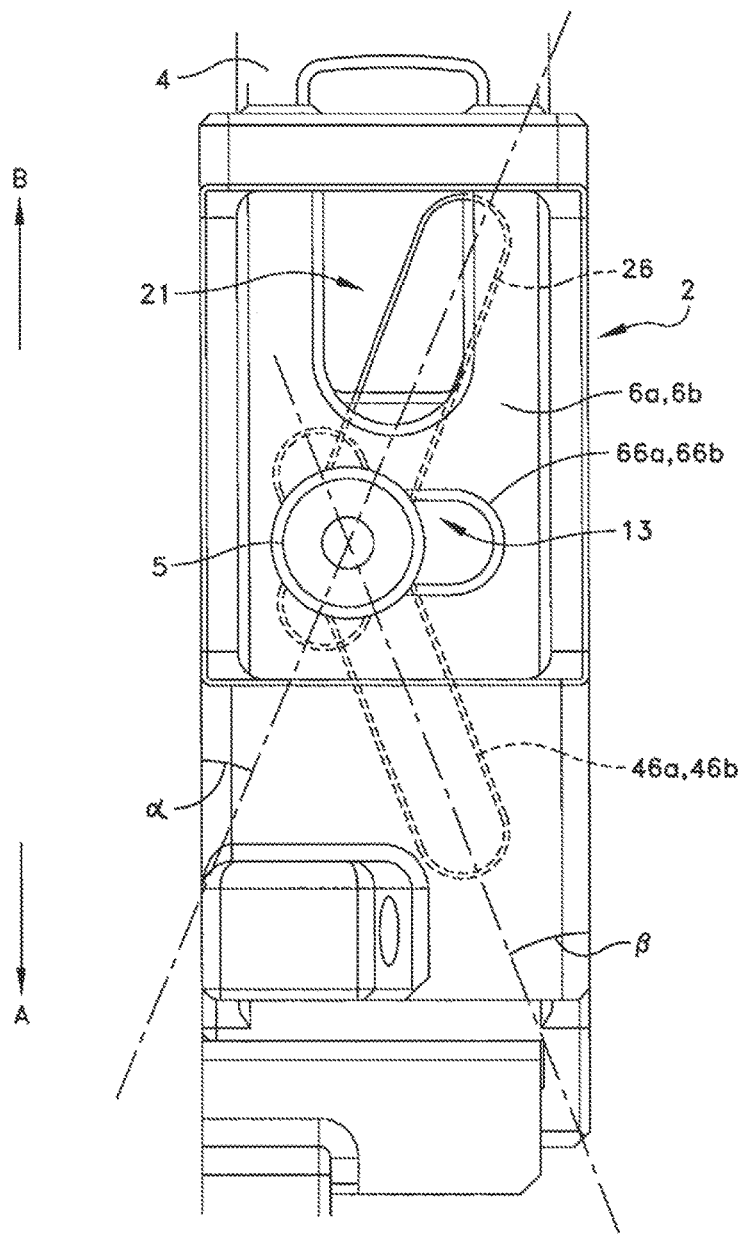
FIG. 7 is a detailed side view of the cross linkage configuration of the sizing caliper in retracted position.
Figure 8:
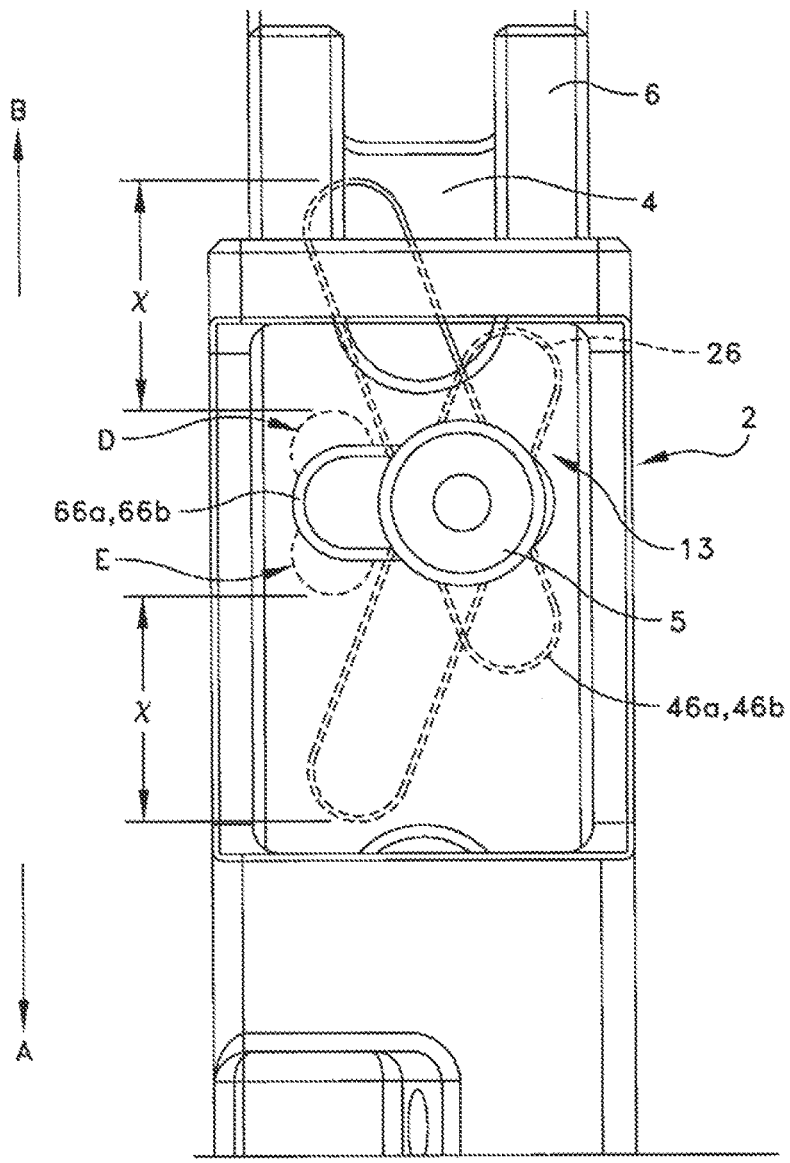
FIG. 8 is a detailed side view of the cross linkage configuration of the sizing caliper in a substantially opened position.

As shown in FIGS. 4 and 5, regardless of whether the sizing caliper 1 is in a substantially closed position as shown in FIG. 4 or in a substantially open position as shown in FIG. 5, the location of the drill guide holes 62a, 62b are always along the midpoint of the A/P dimension 8 of the femur 50. Referring to FIGS. 7 and 8, this aspect of the sizing caliper 1 is accomplished by a cross linkage 13 formed by the caliper body 2, the drill guide body portions 6a, 6b, the stylus tower 4, and a linkage pin 5. FIG. 7 shows the configuration of the cross linkage 13 corresponding to the substantially closed sizing caliper 1 shown in FIG. 4. FIG. 8 shows the configuration of the cross linkage 13 corresponding to the substantially open sizing caliper 1 shown in FIG. 5.

The exploded view of FIG. 6 shows the structure of the individual components of the sizing caliper 1. The cross linkage 13 is formed by the caliper body 2, the drill guide body portions 6a, 6b and the stylus tower 4 assembled with one another and slidably linked to each other by the linkage pin 5. The linkage pin 5 laterally extends through the caliper body 2, the drill guide body portions 6a, 6b and the stylus tower 4. The caliper body 2 has a middle portion 21 that is positioned between the two drill guide body portions 6a, 6b. In the middle portion 21 is provided a first cross linking slot 26 that is oriented at an angle α (see FIG. 7) relative to the longitudinal axis L of the caliper 1 where the longitudinal axis L defines the directions of the sliding motions of the caliper body 2 and the stylus tower 4. In this embodiment, the stylus tower 4 is configured with two extending portions 4a, 4b that extends into the caliper body 2 on either side of the middle portion 21. Each of the two extending portions 4a, 4b is provided with a second cross linking slot 46a, 46b that are oriented at an angle β (see FIG. 7) relative to the longitudinal axis L. The angles α and β of the cross linking slots 26 and 46a, 46b, respectively, are equal which allows the caliper body 2 and the stylus tower 4 to be linearly displaced at an equal rate relative to the drill guide body portions 6a, 6b.

Although two second cross linking slots are provided on the stylus tower 4 in this embodiment for symmetry, one of ordinary skill in the art would understand that functionally, only one of the second set of cross linking slots 46a, 46b is necessary. For example, one of the two extending portions 4a, 4b can be provided with one cross linking slot 46 and a large clearance hole can be provided on the other of the two extending portions 4a, 4b. The clearance hole would be sufficiently large to not interfere with the sliding motion between the linkage pin 5 and the second cross linking slot 46.

Each of the drill guide body portions 6a, 6b is provided with a third cross linking slot 66a, 66b, respectively, that is oriented transverse to the longitudinal axis L. The components, caliper body 2, drill guide body portions 6a, 6b and the stylus tower 4 are assembled together aligning the cross linking slots 26, 46a, 46b, 66a and 66b in an overlapping manner as shown in the side views FIGS. 7 and 8. The linkage pin 5 laterally extends through the cross linking slots 26, 46a, 46b and 66a, 66b.

FIG. 7 shows the configuration of the sizing caliper 1 in a closed or retracted position. Starting with the configuration of the cross linkage 13 shown in FIG. 7, as the caliper body 2 and the stylus tower 4 are drawn apart from one another, the first and second cross linking slots 26 and 46a, 46b corresponding to the caliper body 2 and the stylus tower 4, respectively, move in the directions shown by arrows A and B relative to the drill guide body portions 6a, 6b. As the caliper body 2 and the stylus tower 4 are drawn apart in their respective directions A and B, the angled orientation of the cross linking slots 26 and 46a, 46b cause the linkage pin 5 to slide laterally within the slot 66 in the direction perpendicular to the directions A and B represented by the arrow C. Thus, the linkage pin 5 does not move along the directions A or B and reflects the stationary position of the drill guide body portions 6a, 6b in the longitudinal directions A and B relative to the stylus tower 4 and the caliper body 2.

FIG. 8 shows the configuration of the cross linkage 13 after the caliper body 2 and the stylus tower 4 are drawn apart where the sizing caliper 1 is in a substantially open configuration. The letter D identifies the previous positions of the cross linking slots 46a, 46b and the letter E identifies the previous position of the cross liking slot 26 where the caliper 1 was in a substantially closed configuration shown in FIG. 7. Thus, in the configuration shown in FIG. 8, the stylus tower 4 has been linearly displaced by distance x and at the same time, the caliper body 2 has been linearly displaced also by the same distance x. Thus, the drill guide holes 62a, 62b provided in the drill guide body portions 6a, 6b are always positioned at the midpoint 9 of the A/P dimension 8.

The stylus 3 that positions the A/P dimension 8 of the caliper 1 is in a fixed position 14 in this embodiment but has the ability to rotate or come in from either the left or right side of the assembly, depending on the access of the surgical incision. However, given the variability of the implant, the stylus 3 design can be adjusted so that the measurement position 14 can vary with the size of the implant.

In the illustrated embodiment of the sizing caliper 1, the base portion 7 is a modular unit that removably couples to the caliper body 2. The base portion 7 and the caliper body 2 are configured to couple and decouple using a sliding mechanism. As shown in FIG. 2, the base portion 7 and the caliper body 2 are configured with tongue and groove like structures 78, 28, respectively, to allow the base portion 7 to slide into the caliper body 2. The modular construction allows provision of replaceable base portions each having different angles of external rotation for the final femoral component.

Figure 10:
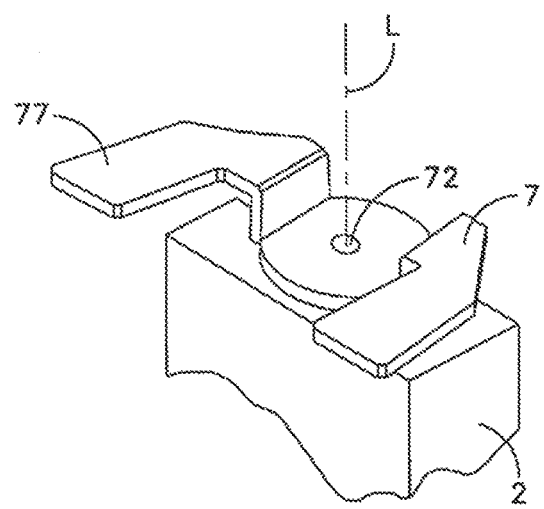
FIG. 10 shows a bottom side view of the sizing caliper showing another alternate embodiment of the coupling configuration between the base portion and the caliper body.

Referring to FIG. 10, in another embodiment, the base portion 7 and the caliper body 2 can be pivotally coupled to each other so that the angle of the base portion 7 can be adjusted without replacing the base portion 7. In this embodiment, the base portion 7 is pivotally coupled to the caliper body 2 by a spindle or a pin 72. Preferably, the spindle 72 is aligned with the longitudinal axis L of the caliper.

Figure 11:
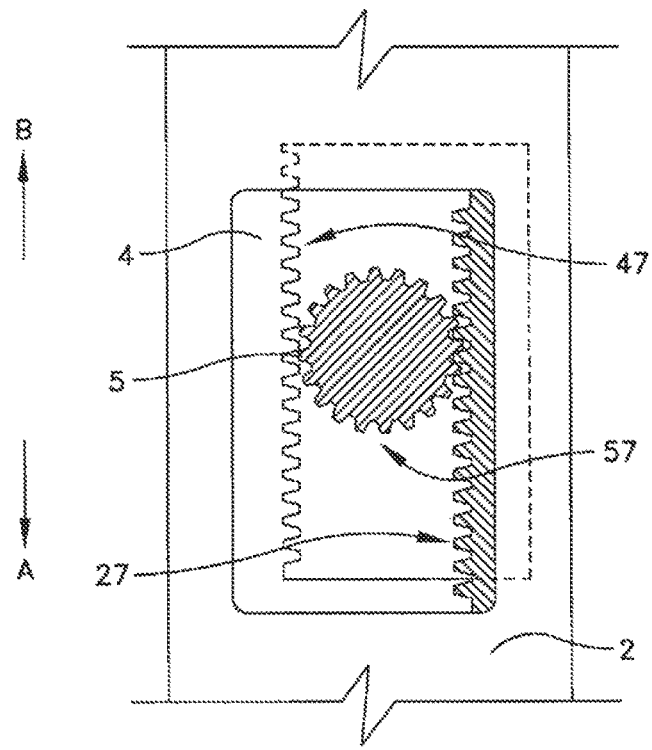
FIG. 11 is a side view of another embodiment of the sizing caliper.

The configuration of the sizing caliper 1 is not limited to the particular embodiment represented by the cross linkage 13 configuration formed by the cross linking slots 26, 46a, 46b, 66a, 66b and the linkage pin 5 discussed above. For example, as shown in FIG. 11, according to another embodiment, a rack and pinion gear assembly can be implemented to achieve the same function of allowing the caliper body 2 and the stylus tower 4 to be linearly displaced in opposing directions relative to the drill guide body portions 6a, 6b at the same rate. In this embodiment, each of the caliper body 2 and the stylus tower 4 is configured with a teeth rack 27 and 47, respectively, and the linkage pin 5 is provided with a pinion gear 57. The linkage pin 5 is captured between the caliper body 2 and the stylus tower 4 by the teeth racks. The pinion gear 57 links the linear motions of the caliper body 2 and the stylus tower 4 and allows the caliper body 2 and the stylus tower 4 to be linearly displaced in the opposite directions A and B at the same rate.

Figure 12:
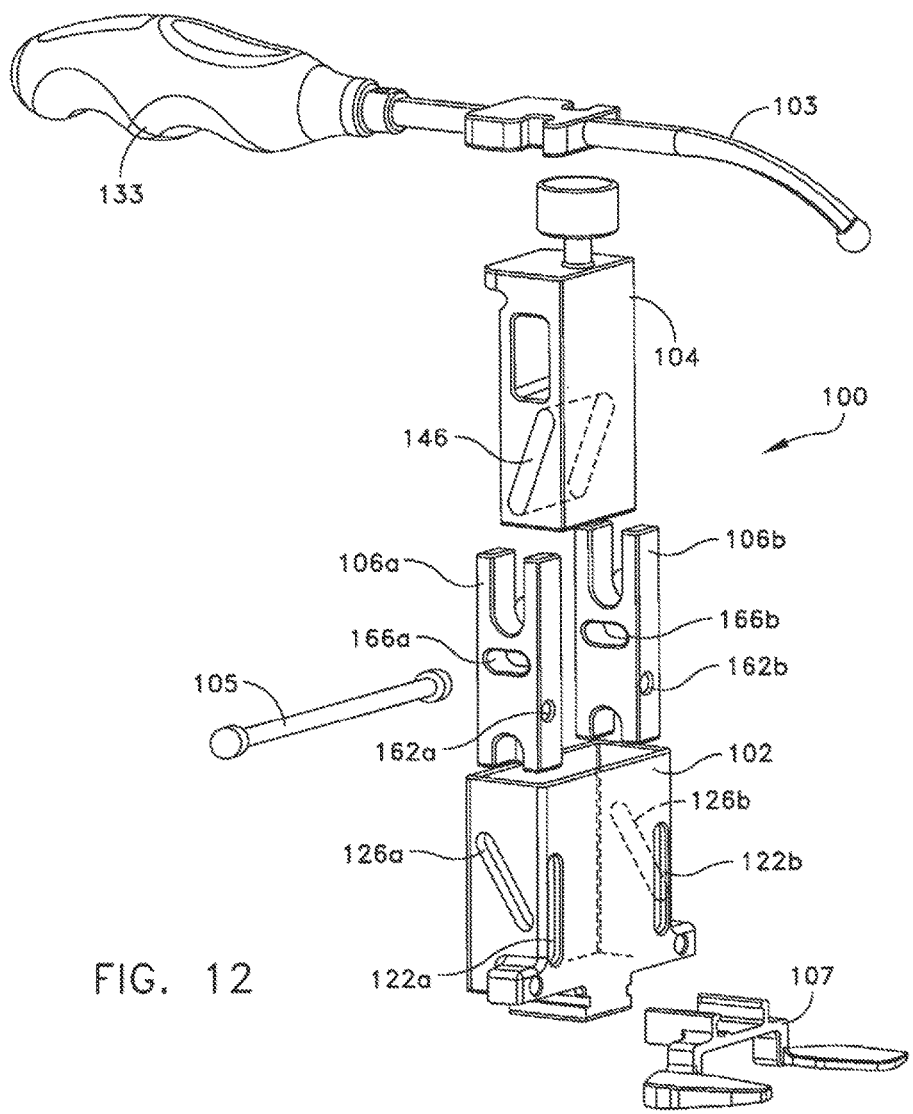
FIG. 12 is an exploded view of the sizing caliper according to another embodiment.

Even in embodiments, where cross linking slots and a linkage pin is used to slidably link the components of the sizing caliper, the cross linkage configuration of the sizing caliper of the present disclosure is not limited to the particular embodiment shown in FIG. 6. FIG. 12 shows an exploded view of a sizing caliper 100 according to an alternate embodiment. The sizing caliper 100 comprises a caliper body 102, drill guide body portions 106a, 106b, and a stylus tower 104. The stylus tower 104, the drill guide body portions 106a, 106b and the stylus tower 104 assemble together and slidingly coupled together by a linkage pin 105 similar to the sizing caliper 1. The stylus tower 104, however, is not bifurcated like the stylus tower 4 of the sizing caliper 1. The stylus tower 104 has a single elongated body with a first cross linking slot 146 (equivalent to the cross linking slots 46a, 46b) provided therein. The caliper body 102 does not have a middle portion where a second cross linking slot is provided in the caliper body 2 of the caliper embodiment 1. Instead, the caliper body 102 is provided with two second cross linking slots 126a, 126b (equivalent to the cross linking slot 26) on its sidewalls. Two drill guide body portions 106a, 106b are provided where each of the drill guide body portions 106a, 106b is provided with a third cross linking slot 166a, 166b (equivalent to the cross linking slots 66a, 66b) and a drill guide hole 162a, 162b. The stylus tower 104 fits between the two drill guide body portions 106a, 106b and those components fit within the caliper body 102. As in the sizing caliper 1, in the caliper 100, the stylus tower 104, the caliper body 102 and the drill guide body portions 106a, 106b are assembled together, thus aligning the cross linking slots 126a, 126b, 146, 166a and 166b in an overlapping manner similar to the overlapping alignment of the equivalent cross linking slots shown in FIGS. 7 and 8. The linkage pin 105 laterally extends through the cross linking slots 126a, 126b, 146, 166a and 166b and slidably links the caliper body 102, the stylus tower 104, and the drill guide body portions 106a, 106b.

Unlike the conventional femoral sizing calipers that reference from either the anterior cortex or the posterior condyles, the sizing caliper of the present disclosure allows the surgeon to reference from the midline of the A/P dimension 8 and thus position the desired component at the midline of the A/P dimension 8. This splits the difference between both previously defined methods and permits optimal positioning of the final prosthesis.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. A sizing caliper instrument for facilitating the selection of a femoral component of a knee prosthesis to be attached to a resected distal end of a femur, said femur having one or more posterior femoral condyles, said distal femur including an anterior cortex, a distal condyle, and a midline of an anterior-posterior dimension, comprising:
    a caliper body having a posterior paddle thereon,
    a drill guide body having a midline reference thereon, and
    a stylus tower having an anterior stylus thereon,
    the caliper body, the drill guide body and the stylus tower slidably linked to each other whereby when the caliper body and the stylus tower are linearly displaced in reference to the drill guide body, the paddle and the stylus are linearly displaced at an equal rate with respect to the midline reference of the drill guide body.

2. The sizing caliper instrument of claim 1, further comprising the drill guide body having two drill guide holes, the drill guide holes located at the midline reference of the drill guide body.

3. The sizing caliper instrument of claim 2, wherein when the stylus tower and the caliper body are linearly displaced in reference to the drill guide body, the drill guide holes remain located at the midline of said anterior-posterior dimension.

4. The sizing caliper instrument of claim 2, further comprising the drill guide body having two spaced apart drill guide body portions, and one of the drill holes is located on each of the drill guide body portions.

5. The sizing caliper instrument of claim 4, wherein when the stylus tower and the caliper body are linearly displaced in reference to the drill guide body portions, the drill guide holes remain located at the midline of said anterior-posterior dimension.

6. The sizing caliper instrument of claim 1, wherein the caliper body, the drill guide body and the stylus tower are slidably linked to each other by a linkage pin laterally extending therethrough.

7. The sizing caliper instrument of claim 1, wherein the stylus is graduated and is slidably coupled to the stylus tower.

8. The sizing caliper instrument of claim 7, wherein a linkage pin extends through the caliper body, the drill guide body portions, and the stylus tower.

9. The sizing caliper instrument of claim 4, wherein the caliper body is provided with a first cross linking slot that is oriented at an angle alpha relative to a longitudinal axis L; the stylus tower provided with at least one second cross linking slot that is oriented at an angle beta relative to the longitudinal axis L; each drill guide body portion provided with a third cross linking slot that is oriented transverse to the longitudinal axis L; the caliper body, the two drill guide bodies and the stylus tower are assembled to be slidably linked to each other by aligning the first cross linking slot, the at least one second cross linking slot and each third cross linking slot in an overlapping manner; the caliper further comprising a linkage pin laterally extending through the first cross linking slot, the at least one second cross linking slot, and each third cross linking slot and slidably linking the caliper body, the two drill guide bodies and the stylus to each other.

10. The sizing caliper instrument of claim 9, wherein the caliper body includes a base portion removably coupled to the caliper body.

11. The sizing caliper instrument of claim 10, wherein the posterior paddle includes a pair of paddles on the base portion.

12. The sizing caliper instrument of claim 9, wherein the caliper body includes a base portion pivotally coupled to the caliper body.

13. The sizing caliper instrument of claim 12, wherein the posterior paddle includes a pair of paddles on the base portion.

14. The sizing caliper instrument of claim 4, wherein the caliper body, the two drill guide body portions, and the stylus tower are slidably linked to each other by a rack and pinion configuration.

15. The sizing caliper instrument of claim 14, wherein the caliper body and the stylus tower are each provided with a teeth rack and the slidable link is provided by a pinion gear that engages the teeth racks.

* * * * *